United States Patent [19]
Taub

[11] Patent Number: 6,083,005
[45] Date of Patent: Jul. 4, 2000

[54] METHOD OF USE OF NATURAL LATEX EMULSION

[76] Inventor: Lawrence Taub, 277 New York Ave., Jersey City, N.J. 07307

[21] Appl. No.: 09/073,189

[22] Filed: May 6, 1998

Related U.S. Application Data

[63] Continuation-in-part of application No. 08/471,272, Jun. 6, 1995, abandoned.

[51] Int. Cl.[7] .................................................. A61C 5/00
[52] U.S. Cl. ........................ 433/215; 433/228.1; 264/16
[58] Field of Search ..................................... 433/215, 213, 433/217.1, 222.1, 228.1, 226; 264/16, 17, 18, 19

[56] References Cited

U.S. PATENT DOCUMENTS

| | | | |
|---|---|---|---|
| 4,024,637 | 5/1977 | Colpitts | 433/191 |
| 4,505,679 | 3/1985 | Gutentag | 433/224 |
| 4,854,875 | 8/1989 | Dziki et al. | 433/213 |
| 5,000,687 | 3/1991 | Yarovesky et al. | 433/180 |
| 5,607,689 | 3/1997 | Checchi | 433/215 |

*Primary Examiner*—John J. Wilson
*Attorney, Agent, or Firm*—M. K. Silverman

[57] ABSTRACT

A method of using latex as a protective separator and release agent between a resin on-lay, in-lay, laminate, or other restorations, and a dental model or tooth to be restored includes the steps of applying the latex to a surface of the dental model preparation by substantially covering the surface area that is to contact and form the restoration, to prevent direct contact of thereto and with the dental model or tooth, while facilitating a mutual release of the elements after curing has occurred. The latex is in the form of an emulsion of about forty to about seventy percent of solids, the solids including a protein material within a water base in which such latex is primarily isoprene butyryl and about 0.04% to about 0.5% percent ammonium hydroxide, to a restoration-forming surface of a dental model of tooth preparation covering that area which is in contact with the resin or other material on-lay or in-lay designed for such fabrication. The method also includes the step of allowing the applied latex to dry to a state of substantial elasticity which state is defined by a change of color of the material within the solids of the suspension of the latex. The method further includes the step of placing a material forming the on-lay or in-lay onto the recess covered with the latex, this preventing direct contact between the restoration and the dental model or tooth structure, while facilitating the mutual respective releases of the restoration and dental model, after curing has occurred.

23 Claims, 10 Drawing Sheets

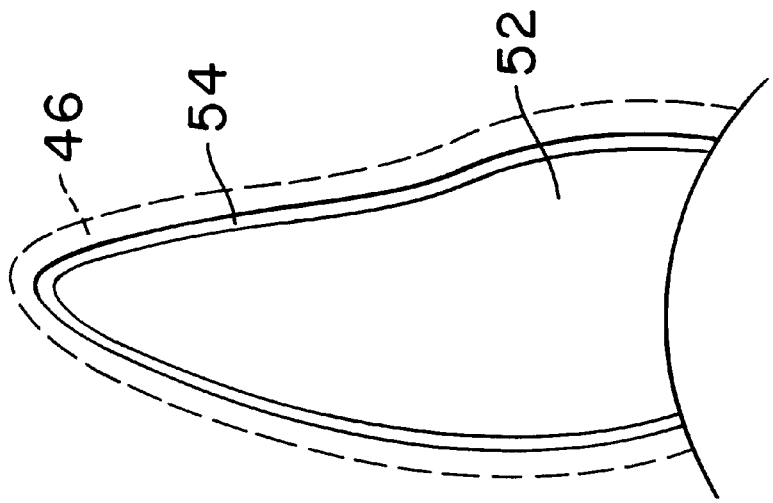
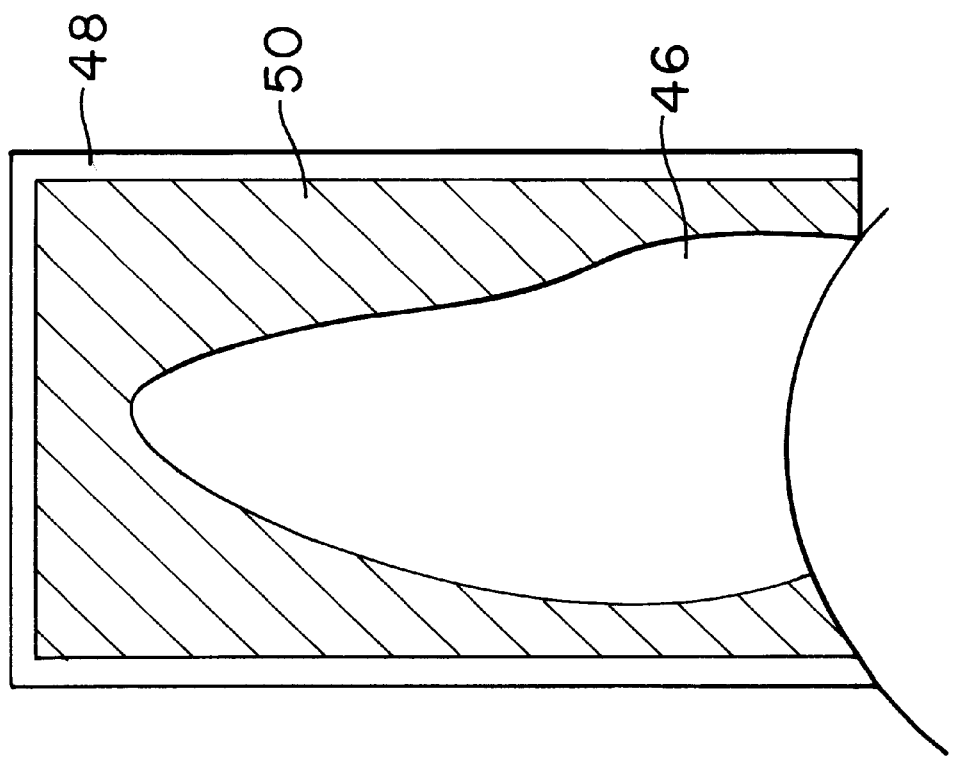

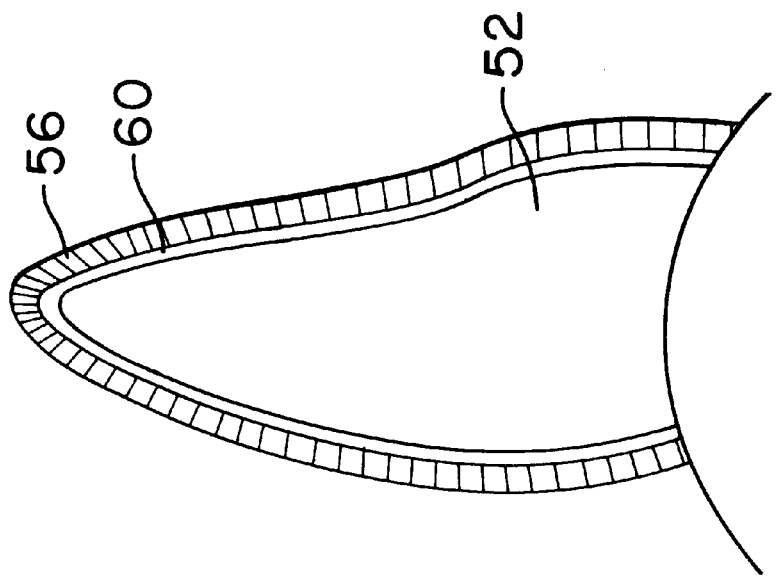
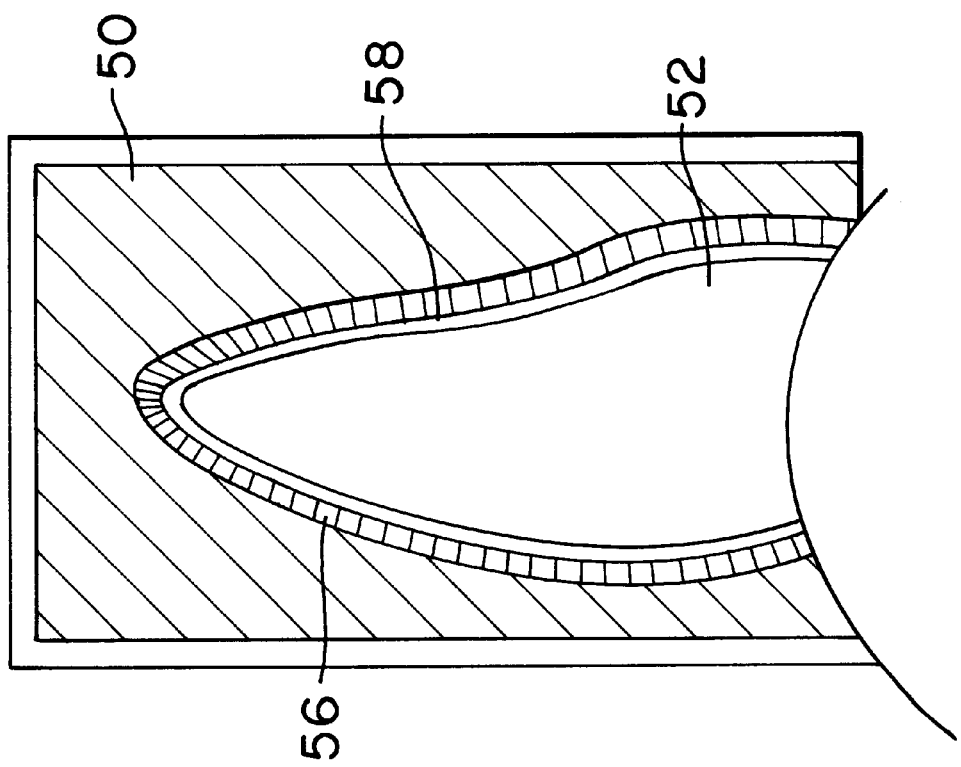

METHOD OF USE OF NATURAL LATEX EMULSION

REFERENCE TO RELATED APPLICATION

This case is a continuation-in-part of Application Ser. No. 08/471,272, filed Jun. 6, 1995 abandoned.

BACKGROUND OF THE INVENTION

This invention relates to a method for applying a natural liquid rubber latex in the relief, separation, and release of dental resins, either directly on a dental model or onto a tooth preparation in the patient's mouth, to thereby allow the separation of a composite resin in-lay, on-lay, crown, splint, provisional or laminate, from the dental preparation, while still allowing a firm fit and allowing room (relief) for dental resin cements to bond the resin on-lay or in-lay to the tooth structure. This provides an improvement in the art, in that the technician or dentist can use such a separator to effectively form a composite resin in-lay or on-lay in a tooth preparation or a wax pattern of the same, in the process of creating a metal casting or pressed ceramic replication of such on-lays or in-lays, while protecting the preparation and effecting its removal without damage during removal of the on-lay or in-lay from the model or tooth preparation. This invention also permits a space to be created on the internal portion of the on-lay or in-lay, allowing a relief for the cementing material to adhere to the on-lay or in-lay and to the tooth, while still enabling an exact fit of the in-lay or on-lay into or onto the patient's tooth. This invention thereby permits the latex to be easily peeled from the model, tooth preparation, composite resin, or wax pattern to avoid the need to clean either, once separated for use or refitting.

This invention also allows the technician or dentist to form an extra space or well during the formation of a dental bleaching tray, for dental bleaching, by using the latex separator to create a larger volume or space on the labial surface of the model's tooth area to be bleached, this for the application of such dental bleach to the teeth while still allowing a firm fit of the dental tray or vacuum form to the teeth. Unlike polymeric materials, used for the same purpose, that may become permanently bonded to the model in the case of bleaching procedures, the latex is peeled off of the labial surface of the model or from inside the bleaching tray.

The prior art, as is known to the inventor, entails the use of a lubricant, such as petroleum jelly, to coat the dental model preparation before the resin or other material is placed into it, or to coat the tooth preparation before the resin is placed onto the tooth to create the on-lay or in-lay before it is placed onto the tooth, or do nothing at all first and then abrade with wheels, sandblasting, or the like, the underside surface of the resin on-lay or in-lay to create room. Thus, the lubricant precludes the on-lay/in-lay from damaging the preparation during removal, while still allowing a technician or dentist to easily remove the on-lay or in-lay from the model, or to loosen the on-lay/in-lay from tooth. However, lubricants can leave a coating upon the on-lay/in-lay and the dental model or tooth, requiring cleaning in order to re-fit. Furthermore, such lubricants are difficult to apply evenly and, therefore, may result in uneven film application of cement which bonds the on-lay/in-lay to the tooth, and lubrication can leave residual film that may interfere with or reduce subsequent bonding procedures.

This invention also protects against the heat generated during the curing of certain dental resins, either during curing by auto-polymerizing, chemical curing, light curing, or other means to affect the dental pulp, damaging or destroying the tooth pulp, by acting as a thermal insulator between the curing resin and the tooth preparation, during the fabrication of provisional resin restorations or composite (all types) resin restoration. The temperature rise caused by polymerization of methyl methacrylate resins, which can exceed 50 degrees Fahrenheit in the curing process, will cause irreparable damage to the tooth pulp.

None of the above, or other art known to the inventor, addresses the above problems, that is, the separation of a composite resin on-lay or in-lay from dental model, or tooth structure by preventing contact therebetween and allowing ease of separation of the on-lay or in-lay from the model or tooth, and the peeling away of this film separator/spacer.

Further prior art known to the Applicant is reflected in U.S. Pat. No. 5,000,687 (1991) to Yarkovesky, et al, entitled Winged Dental Bridge and Process of Manufacturing the Same. However, while Yarkovesky and the instant invention both relate to the art of dental restorations, Yarkovesky is directed to a structure and a method of manufacture. In distinction, Applicant's invention is directed to a method of use of a special latex, as defined below, as a protective separator and release agent for dental on-lays and in-lays. Accordingly, while the respective art areas are related, the actual respective inventions have nothing to do with each other. It is further noted that the instant invention relates to the area of clinical dentistry, not to that of polymer chemistry. Accordingly, Applicant's within use of a certain latex, having therein a special-purpose suspension or emulsion of solids, is to be viewed in terms of the knowledge of the prior art relative to the application of such an elastomeric and protein containing latex, in the particular area of clinical dentistry addressed by the present invention.

A further application of the instant invention is the placing of white rubber latex film on the model of the tooth preparation allowing it to set or dry, and then placing a die spacer over the latex film in the fabrication of a cast metal or porcelain restoration. Said die spacer, after use is completed, may be completely peeled off of the die preparation, together with the latex film, leaving a clean preparation, this producing a peelable die spacer.

In a another application of the instant invention, by placing the latex rubber over the model of a tooth preparation having previously been coated with a prescribed dentin colored die spacer, and said latex rubber film is allowed to dry clear. The exposed dentin colored die spacer is now useful in color or shade determination of a composite resin (hybrid or otherwise), or other materials used for this or other purposes, for veneers, laminates, on lay or in lay, crowns, or other restorations, placed over it. The protective film allows transmission of the shade of dentin colored die spacer while preventing the composite resin from bonding to the die spacer when the composite resin is curing or has cured. Thereafter the die spacer is removed from the model's preparation.

SUMMARY OF THE INVENTION

A method of using latex as a protective separator and release agent between a resin on-lay, in-lay, laminate, or other restorations, and a dental model or tooth to be restored includes the steps of applying the latex to a surface of the dental model preparation by substantially covering the surface area that is to contact and form the restoration, to prevent direct contact of thereto and with the dental model or tooth, while facilitating a mutual release of the elements after curing has occurred.

It is an object to provide an effective method of protective separation of the on-lay, in-lay, or restoration from a tooth to be restored, which allows the restoration to be easily removed from the tooth or model after curing of the restoration has occurred.

It is a further object of the invention to provide a more effective method of protective separation of the resin on-lay or in-lay, and a dental model or tooth in which the material thereof may be easily cleaned and removed from the on-lay or in-lay, and dental model or tooth.

It is a further object to provide a more effective way for building up of space on a model to create a well for bleaching solution or the model, allowing bleaching tray to be formed by currently available means, such as by a vacuum former with such extra space provided.

It is a still further object of the present invention to provide a more effective method of protective separation of dental on-lays, in-lays, and other restorations, from dental models, or tooth structure which allows a space to be formed between the on-lay or in-lay and the patient's tooth, to allow cementing material to be placed in said space to adhere the on-lay or in-lay to the tooth, while still permitting an exact fit of the on-lay or in-lay to the tooth. This enables the majority of the resin shrinkage from taking place before it is bonded to the tooth structure.

The above and yet other objects and advantages of the invention will become apparent from the hereinafter set forth Detailed Description of the Invention and Claims appended herewith.

BRIEF DESCRIPTION OF THE DRAWINGS

FIGS. 1 through 4 show the steps in the application of the method for the protection of the surface of a tooth preparation when a restorative dental resin is to be placed thereover.

DETAILED DESCRIPTION OF THE INVENTION

Figure 7:
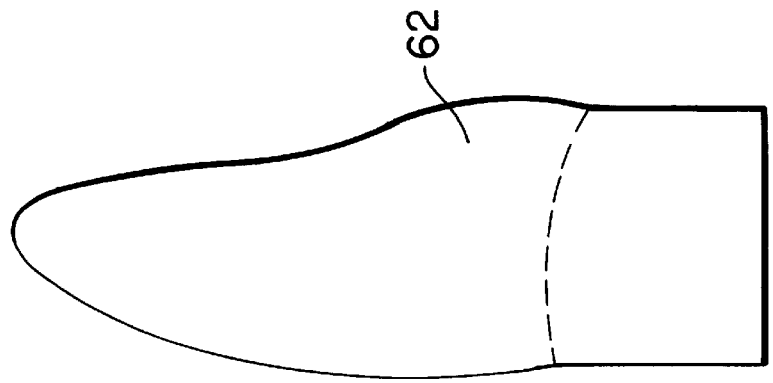
FIGS. 5 through 7 show the application of the present method in the application of the latex emulsion over a tooth die followed by application of a die spacer over the latex emulsion.

In the present invention a natural latex rubber emulsion is used as a protective separator, release agent and die spacer between (a) dental composite resin on-lays and in-lays, crowns, splints, laminates and provisionals (herein referred to resin restoratives) and (b) dental models and tooth preparations to be restored. The natural latex comprises primarily isoprene butyryl solids and about 0.02% to about 0.5% ammonium hydroxide, this as an aqueous emulsion in the range of about 30% to 70% solids in water, with about 40% to 45% solids being optimal. The latex is therefore in a liquid form, which dries to a resilient rubbery consistency upon evaporation of the water and exposure of the latex solids to air. It is to be understood that other forms of latex may also function within the scope of the present method.

The liquid latex is spread evenly, ideally with a brush or dental applicator, over the dental model or tooth preparation, completely covering the surface areas of the dental preparation which will contact the composite resins to form the on-lay or in-lay, crown, or other restoration to within 0.5 mm short of the preparation's margins. The latex is then allowed to dry to a rubbery consistency before the resin is placed onto the preparation or model. The thin liquid film will then dry cure to a film thickness of at least 8 microns. This further ensures that damage by contact will not occur between the composite resin on-lay, in-lay crown, or other restoration thereby formed, and the dental model or tooth preparation, that is, damage that could otherwise occur during release or removal or such on-lay or in-lay from its substrate.

It is to be understood that the attachment of the latex film to itself must be much greater than the attachment of the film to the substructure or resin placed and cured over the preparation or model. Upon drying, a cured film of said latex will stretch like a very thin rubber latex glove or balloon, although not as thick as such films. Such curing corresponds to the aspect of the present method in which "substantially resiliency" or elasticity of the latex is accomplished.

The term "dry cure" as used herein refers to the fact that in establishing the drying of said suspension of latex, it releases water as a result of surface drying or evaporation and, contemporaneously therewith, a protein action cures the balance of the solids as well as the remaining water into a single film. The protein therein binds with the water as it begins to dry, this setting up the curing process. Application of a chemical accelerator, heat, the blowing of air thereon, or light activation accelerates the curing process. However this means is not employed to the point of baking. The curing point of substantial resiliency/elasticity, is indicated by a change in color of the liquid resultant from the curing of the protein component of the solids of the 30 to 70 percent suspension of solids of latex within the water base. Depending upon the type of colorant or lack thereof different changes in color will occur. For example, the liquid in an uncured state may appear as an opaque light pink liquid film which, upon curing, becomes a translucent deep red film. This optical change indicates that sufficient drying has occurred and that the desired state of substantial resiliency/elasticity has been reached, such that the next step in the instant method can begin.

In the use of other colorants (or lack thereof), an opaque white will cure into a completely clear film, an opaque beige film will cure into a translucent amber, and an opaque blue will turn into a translucent dark blue. Accordingly, in all forms the cured latex film is indicated by a substantially translucent or darker appearance. These colorants can be of any shade, but not limited to the above colors.

After the latex rubber liquid has cured into a thin film layered latex, the composite resin or other material used for making the on-lay, in-lay, crown, or other restoration, is placed into or over the preparation and shaped or sculptured by the dentist or dental technician to form the resin on-lay, in-lay, crown, splint or other restoration, which is then cured or hardened by such means as are currently available, the same including, but not limited to, light curing, heat curing, combinations thereof, or self-curing. The cured restoration is removed in the preparation in order to remove the latex film the thereunder. After removal of the latex film, the finalized restoration is then placed back into firm contact with the dental model or tooth, and can be laid or removed without damage to the dental on-lay, in-lay or tooth preparation, leaving enough space uniformly between the preparation and the resin restoration for cementation. The latex will also fill in minor undercuts that may exist within the preparation.

Figure 9:
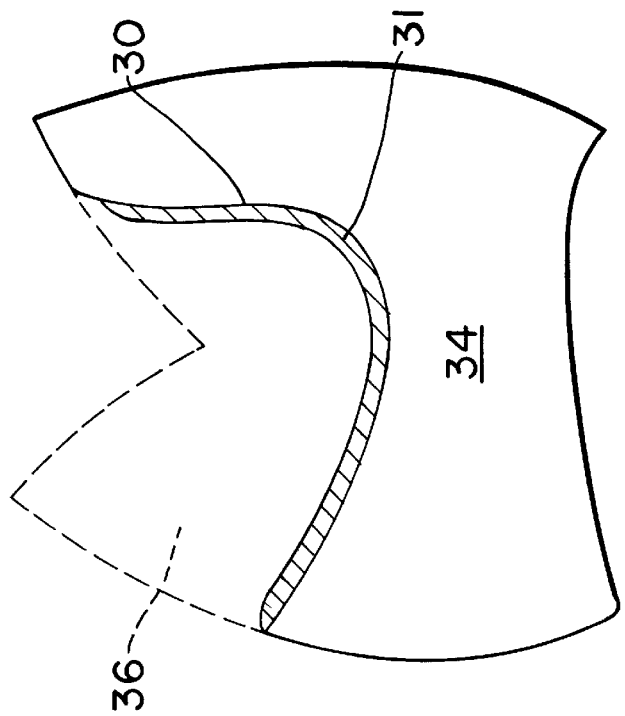
FIGS. 8 and 9 show the application of the method wherein the latex emulsion is applied to an inside contact surface of a preparation of an on-lay or in-lay prior to placing a restorative resin thereover, this for ease of removal of the resin and to create a space or relief for resin cement.
Figure 8:
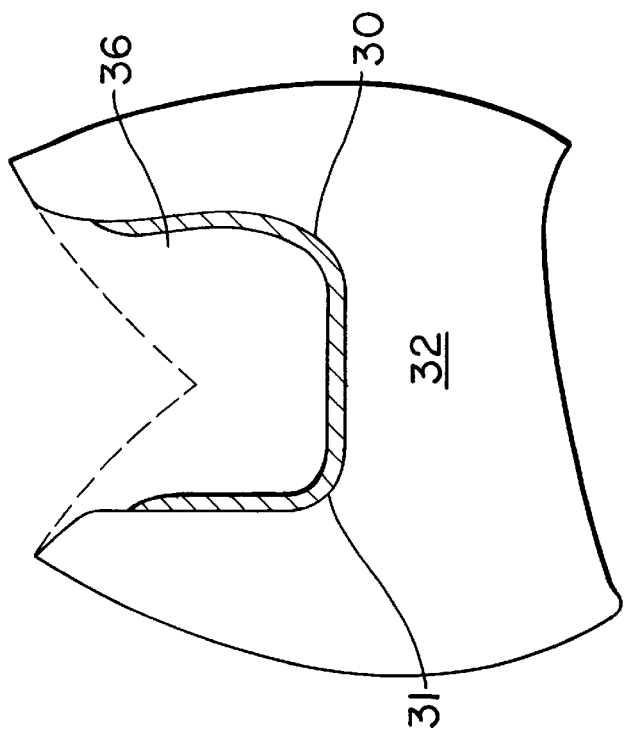

In one embodiment of the inventive method (see FIGS. 8 and 9), latex 30 is applied to a contacting or recess surface 31 of the dental model or preparation of an in-lay 32 or on-lay 34, completely and evenly coating the surface 31, prior to placing thereon a composite restorative resin 36, thus forming the on-lay or in-lay onto or into the dental model or preparation.

Figure 11:
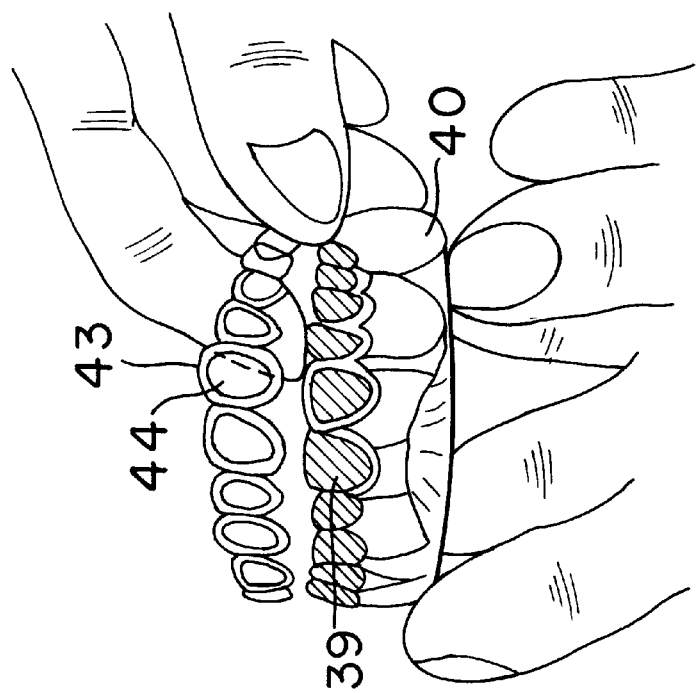
FIGS. 10 and 11 show the method of use of the latex emulsion in connection with a tooth bleaching tray.
Figure 10:
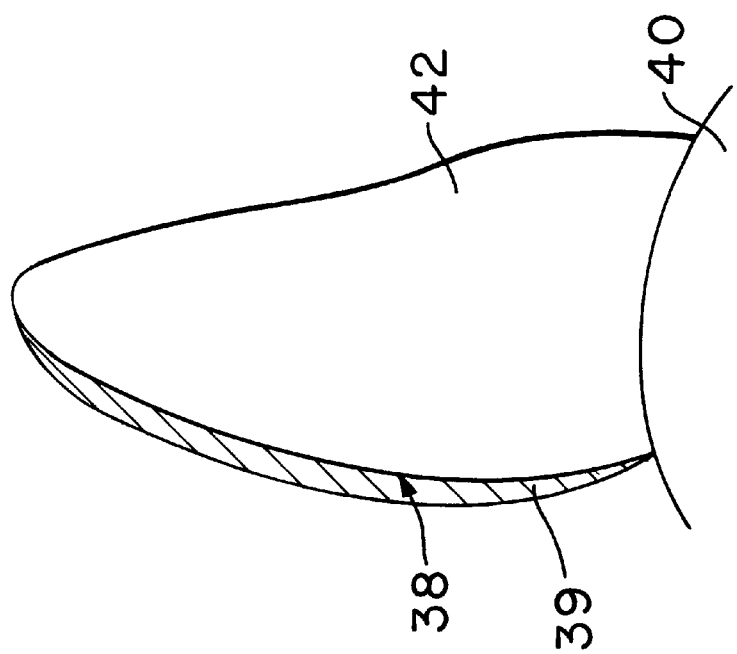

In another embodiment (see FIGS. 10–11) latex 39 is applied heavily between about 0.2 and 1.0 mm thickness or as multiple thin layers, to a labial tooth surface 38 of a model 40 of the teeth 42 to be bleached prior to the use of a dental bleaching appliance tray 43 upon said model 40, and permitting the latex to dry cure on its own or with the aid of heat from an oven, radiant source lamp, application of an air spray, an accelerant chemical, or an actuator in the case of curing or rapid polymerization, to thereby provide space for the bleaching agent on the teeth. This material allows a vacuum forming tray or other manufactured bleaching tray to be formed over the model and removed from the model with an imprint of added space or reservoir 44 for the latex rubber without the permanent attachment of the spacer to the tray or model, or discoloration of the same.

In order to clean the on-lay, in-lay, resin restoration, dental model, or tooth of the latex, one need only peel the curved latex film from the respective surfaces. The latex easily and uniformly peels from the surfaces of the model, tooth or resin and leaves no residue, that might contaminate subsequent bonding procedures.

The latex's removal, in being peeled out of a recess, creates a space between the on-lay, in-lay, laminate, crown or dental bleaching tray, and tooth upon which the restoration or tray, will fit. Said space allows the use of cementing material between the on-lay or in-lay or resin restoration, and tooth for purposes of adhesion, while still allowing an exact fit. This space created in the dental bleaching tray allows the liberal and sufficient use of dental bleach material (gel) to whiten the patient's teeth.

Another application of the present method of use of natural latex is shown in the views of FIGS. 1 through 4. Therein is shown a technique for making a resinous provisional restoration from an impression taken of the patient, or from a vacuum-formed matrix from a model of the patient's teeth. More particularly, shown in FIG. 1 is a tooth 46 to be restored in which an impression chamber 48, holding an impression material 50 is used to take an impression of the unrestored tooth 46. Thereafter, tooth 46 is reduced to create tooth preparation 52 (see FIG. 2) in which the original tooth geometry is shown in dotted lines 46. After such tooth reduction, a latex film 54, that is, more particularly, the above-referenced aqueous natural latex emulsion, is applied to the surface of the tooth preparation 52, and allowed to dry. Thereafter (see FIG. 3) a restorative dental resin 56 is applied into the impression 50, which is placed over the latex 54 coated preparations of the tooth or dental model of same and the provisional is fabricated as is recommended by resin manufacturers. During this step, the use of said film of natural latex emulsion provides a prophylaxis of the tooth dentin (of preparation 52) from cure-related thermal, general toxic, and pressure effects of resin 56 and, particularly, from a component thereof known as the monomer of the resin. Accordingly, a number of important health and safety advantages are accomplished through the use of latex film 54 between the tooth preparation 52 and resin 56.

Shown in FIG. 4 is the attachment of resin 56 to the tooth preparation 52 through the use of a temporary or permanent cement 60. Prior to cementation, the latex film 54 is readily peeled away from the hardened resin 56 which, therein, leaves room for placement of cement 60, thereby performing a relief function.

It is to be appreciated that resin 56 may comprise any dental resin including, without limitation, acrylic, composite-inclusive, urethane-based, and bio-ceramic resins.

Film 54 is preferably applied to a thickness of least eight microns but less than 30 microns. Further, prior to application of the restorative resin 56, the latex emulsion is permitted to dry or cure to a state of substantial elasticity prior to application of said restorative resin 56. Therein, curing occurs through evaporation of water of the aqueous emulsion of the natural latex. Therein, a satisfactory point of cure for purposes of said substantial elasticity is defined by a change of color of the latex.

Figure 6:
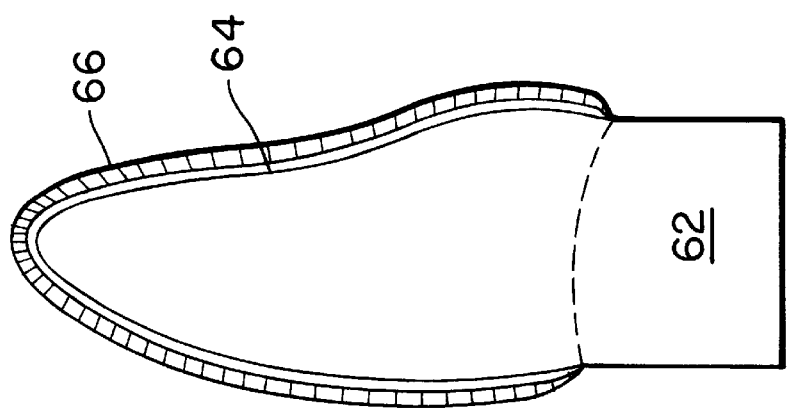
Figure 5:
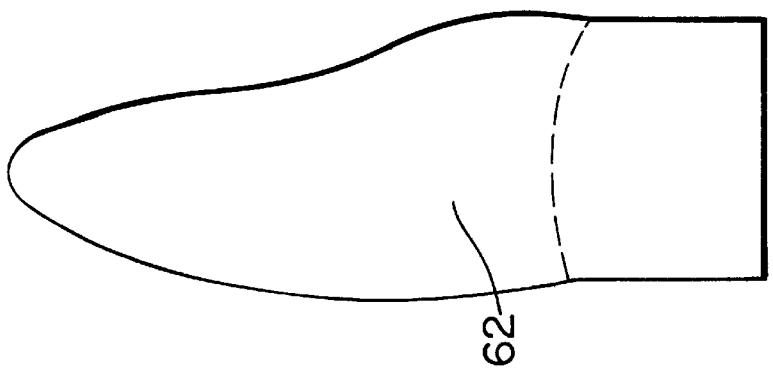

A further application of the present method is shown in FIGS. 5 through 7, this application known as the "peelable die spacer" method. Therein, there is applied, to a tooth die of a model 62, a layer 64 of latex emulsion. Thereover is applied a die spacer 66. As in the prior application of the method, the latex emulsion is permitted to dry or cure to a state of substantial elasticity prior to application thereover of the die spacer. Further, the latex emulsion must be applied to a thickness of at least eight microns. It is further noted that curing of the film of latex may be induced through the use of various accelerating means, as referenced above. It should be noted that in the method of FIGS. 5 through 7 the latex film 64 is capable of performing both the release and separation functions of die spacer 66 as is more fully set forth below. FIG. 7 indicates that after waxup, the post-restoration is invested and a crown is formed, which is put back onto die 62 with die spacer 66 to thereby check the fit of the proposed restoration and to make whatever mechanical adjustments may be necessary. Thereafter die spacer 66 is peeled away together with the latex film 64 to clean the die spacer off of the model.

Figure 13:
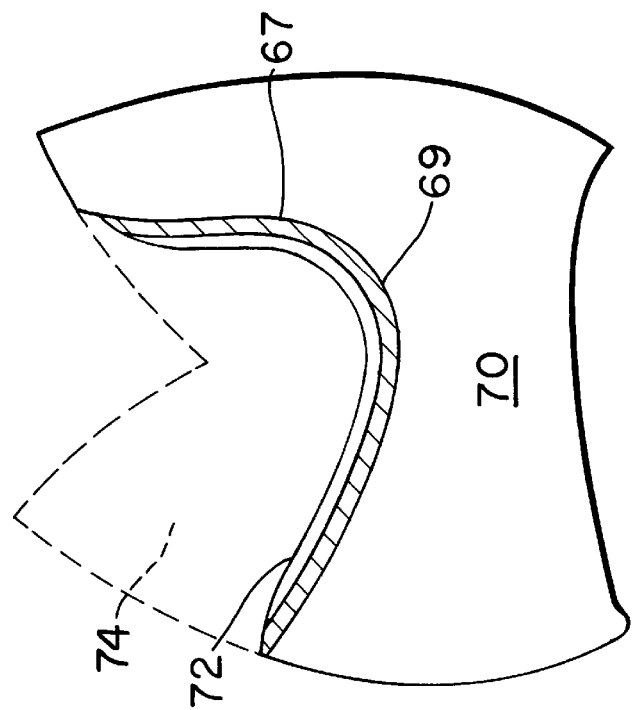
FIGS. 12 and 13 show use of the present method in which the natural latex is used as a protective separator, release agent, or spacer between a model of a tooth preparation coated with a specified or prescribed dentin colored die spacer and a resin used in the formation of a translucent dental restoration such as an on-lay or in-lay (shown here) as well as all resin restorative procedures including laminates, crowns, and other restorations where the body of the resin used is translucent or transparent enough that the dentin shade of the preparation influences the shading of the resin above.
Figure 12:
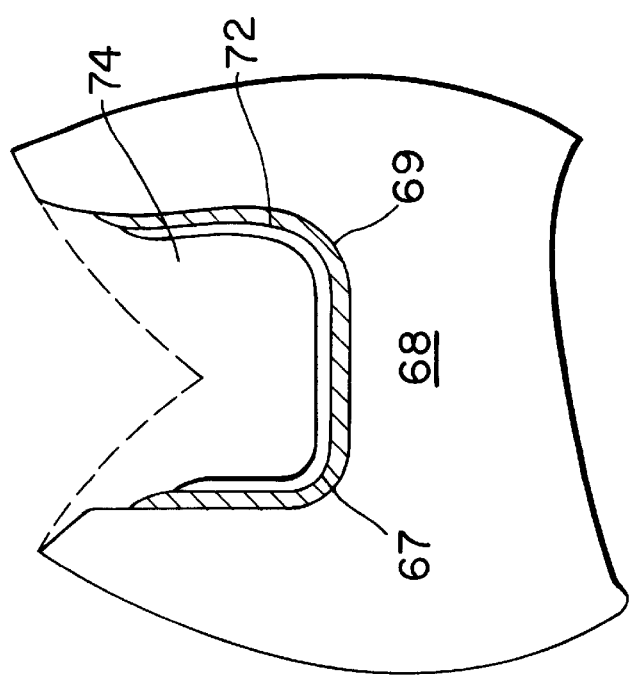

In FIGS. 12 and 13 is shown a further embodiment of the instant method in which the aqueous natural latex emulsion is used as a protective separator, release agent, and/or spacer between a model of a tooth preparation and a resin used in the formation of a translucent dental on-lay, in-lay, crown, bridge, provisional, laminate or other restoration. The method of the embodiment of FIGS. 12 and 13 more particularly comprises the steps of applying a layer of a prescribed dentin colored die spacer 67 to a recess or contact surface 69 of an in-lay 68 or on-lay 70. Thereafter, a film or layer of opaque white natural latex 72 (comprising an emulsion of about 30 to about 70 percent natural rubber solids) is applied over said dentin color die spacer 67. Thereafter, the latex film 72 is permitted to dry to a clear transparent state. A translucent restorative resin 74 is then applied over the latex layer 72. Thereby, coloration of the die spacer (which is representative of the dentin color of the patient's tooth) is visible through the restorative resin, this enabling a technician or dentist to better judge the accuracy of the color of the resin built up over the latex and preparation, the same prior to removal of the cured resin from the preparation, which removal is facilitated through the use of said layer of latex. It is noted that said emulsion will preferably have about 40 to about 45 percent of natural rubber latex solids therein. As in prior applications of the present method, the latex 72 is applied to a thickness of at least eight microns and, as well, the latex layer is permitted to cure to a state of substantial elasticity, this defined by a change of the color of the latex from white to transparent, before the translucent restorative resin 74 is applied.

With reference to FIGS. 14 through 18, there is shown a further embodiment of the present invention showing the use of the natural latex emulsion as a protective separator, release agent and/or spacer between a translucent resin 82 used in the formation of a translucent restoration and a tooth die 76. As is shown, said die 76 which is covered by a dentine colored die spacer 78 which in turn is covered by a film or layer of clear natural latex 80, as above defined.

Figure 15:
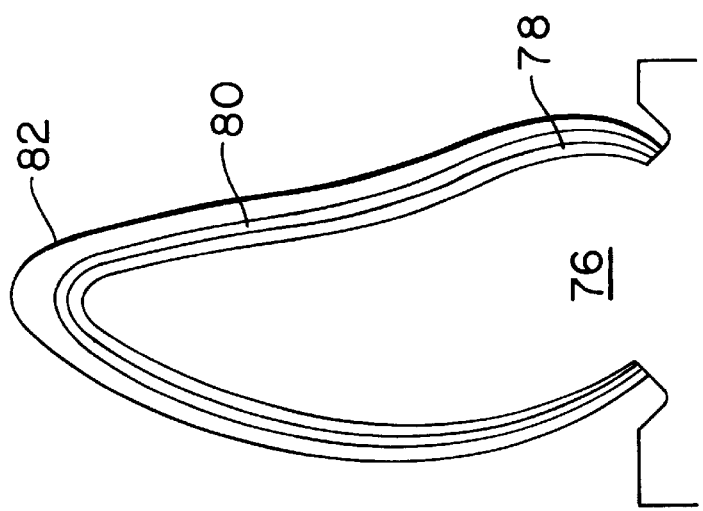
Figure 14:
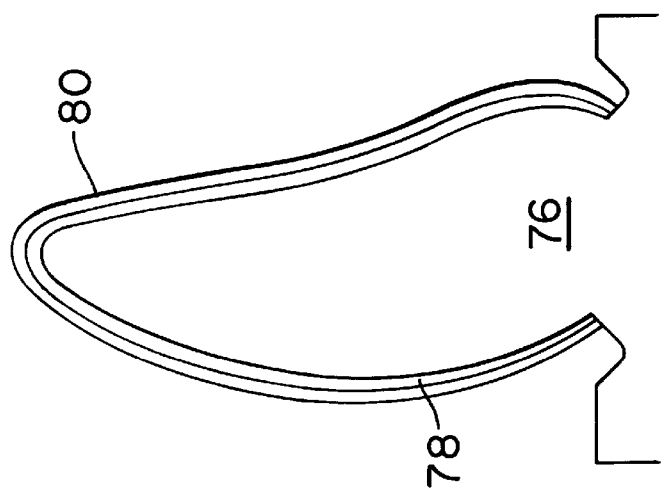

In FIG. 15 is shown the application of the translucent restorative resin 82 over the clear natural latex 80.

Figure 16:
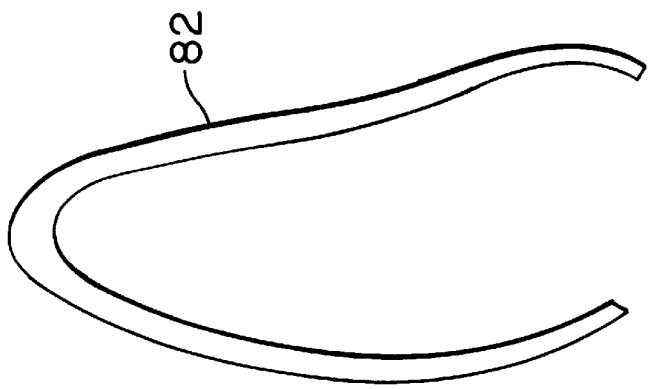
FIGS. 14 through 18 show the steps in the application of the method as a protective separator, release agent or spacer between a translucent resin used in the formation of a restoration and a tooth die having a dentin colored die spacer applied over the die.
Figure 18:
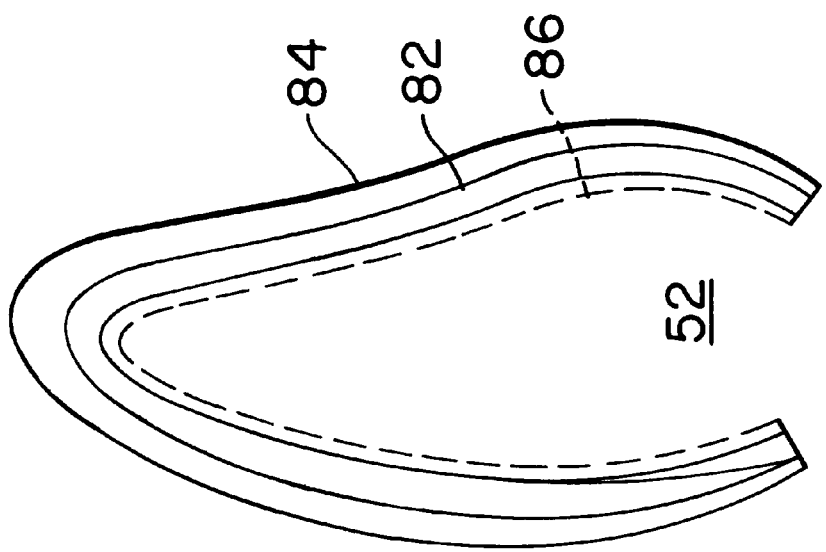
Figure 17:
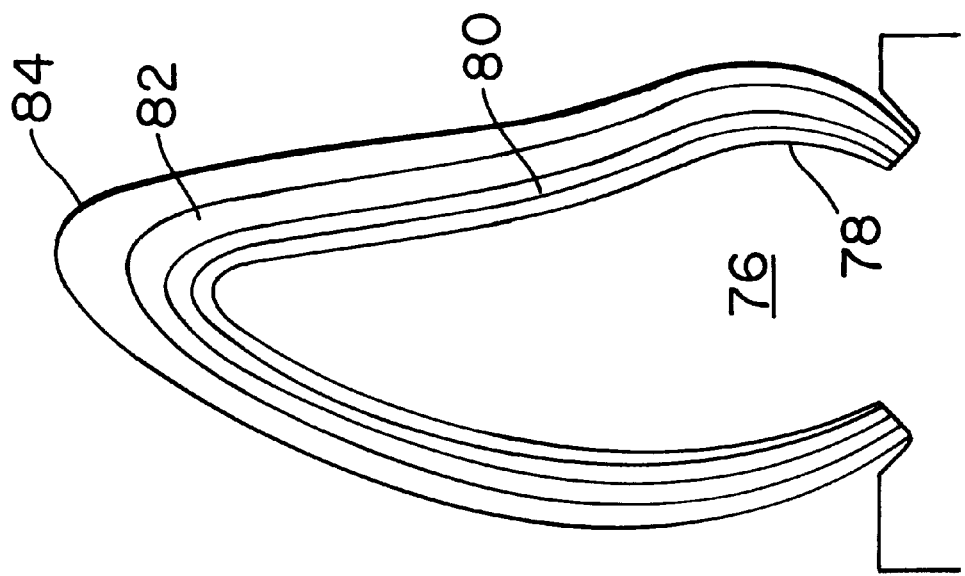

In FIG. 16 is shown the cured translucent resin 82 over the clear latex 80. The two oppositely directed arrows between FIGS. 16 and 17 indicate that the translucent resin 82 may be replaced onto the die 76 if it is necessary for the technician to judge the accuracy of the color of the resin relative to the dentin colored die spacer 78. This is more fully shown in FIG. 17 in which the shade of the die spacer 78 may be seen through a clear or translucent resinous substructure 82 thereby influencing extrinsic shading of the restoration 84 to properly match the intrinsic or dentin shade of the tooth preparation. The application of the enamel or extrinsic shading is indicated by resinous built-up material 84 in FIG. 17. In FIG. 18 is shown the removal of the structure of FIG. 17 from the tooth die 76 and the bonding thereof through the use of a translucent bonding resin 86 to the tooth preparation 52.

Figure 19:
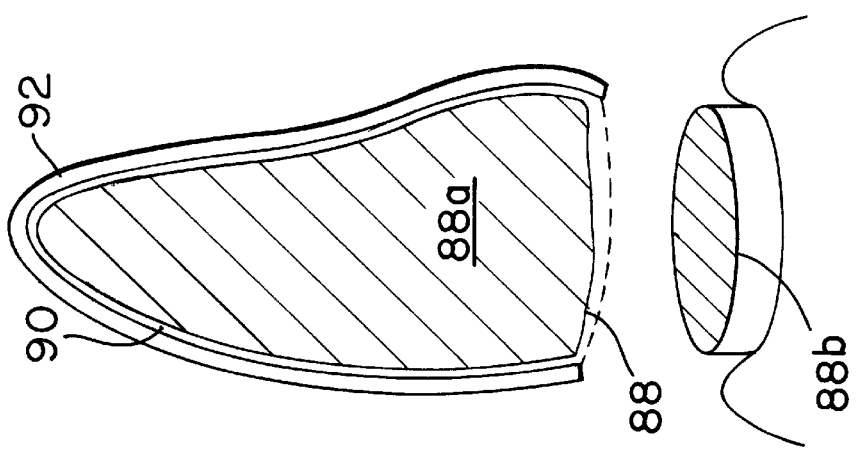
Figure 23:
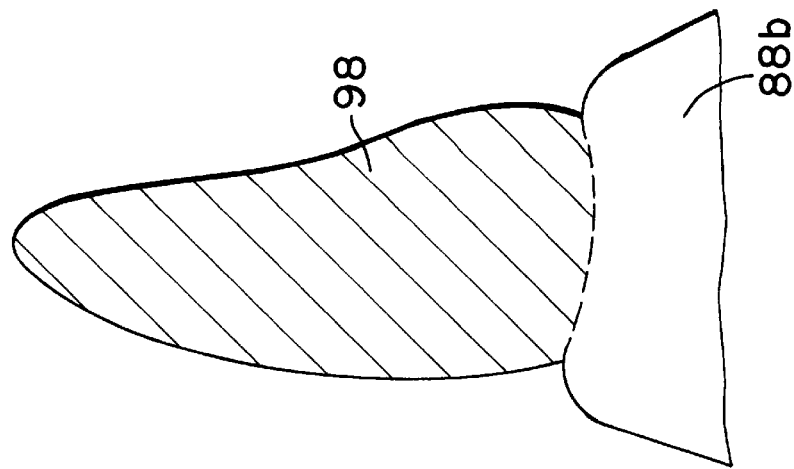

With reference to the views of FIGS. 19 through 23 is shown application for the present method to the re-building of a damaged natural tooth preparation such as a dental crown. Therein, in FIG. 19, is shown a fractured tooth 88a consisting of upper portion and lower portion 88b. Further shown in FIG. 19 is cement 90 which interfaces the surrounding surfaces of the broken tooth with a dental crown 92.

Figure 20:
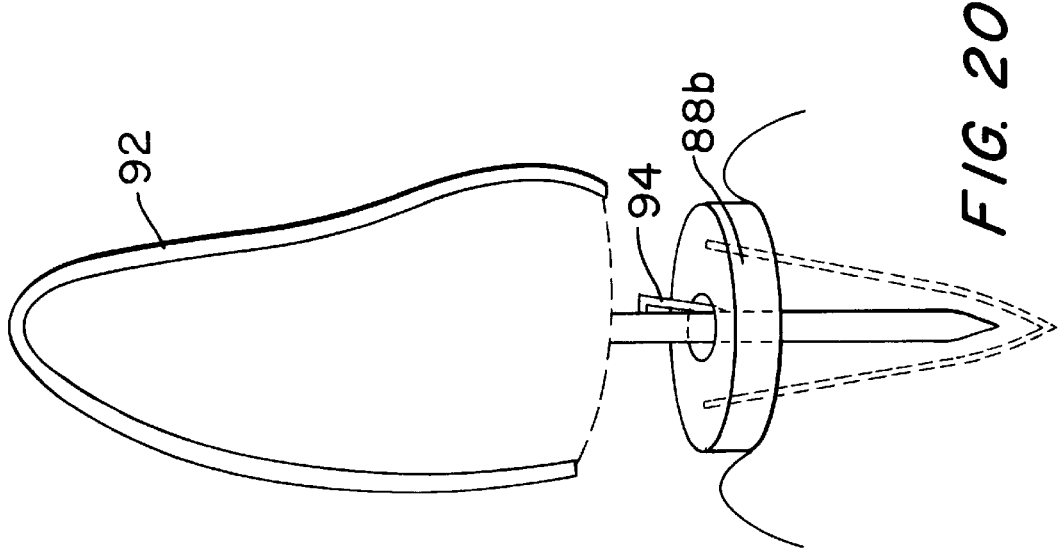
FIGS. 19 through 23 show the application of the present method in the rebuilding of a natural tooth preparation having a broken or damaged aspect and for salvaging or saving a ceramic or metal crown onto which a broken tooth had been previously cemented.
Figure 21:
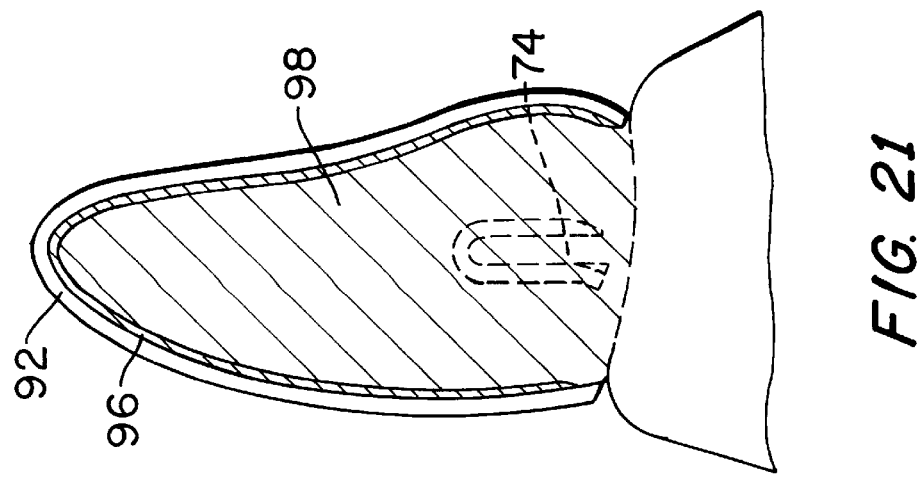

Shown in FIG. 20 is the removal of a tooth and cement from a crown 92 and a completed fabrication of a post 94, or core in lower tooth portion 88b. In FIG. 21 is shown application of a layer 96 of the natural latex emulsion which dries to the interior surfaces of the crown after the removal shown in FIG. 20 has been accomplished. Thereafter, a dental restorative resin or cement 98, such as self-cure or two part resin, is applied inside the crown. The crown is placed back over the post 94 or core, adjusted properly for fit, seating and occlusion, and the resin/cement is allowed to set or cure within.

Figure 22:
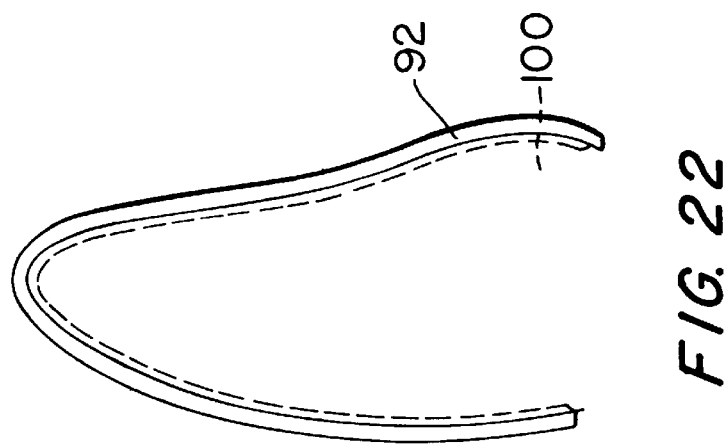

As noted in FIG. 22, after the core built up material, i.e., resin cement 96 has cured, the crown 92 is removed from the newly formed preparation. Therein the latex film 96 enables separation between the crown 92 and the cement/resin 98. Thereafter, the latex film 96 is peeled away and a second cement 100 is placed inside the crown 92. Thereafter the crown 92 is seated upon the preparation (see FIG. 23) and cemented thereto, that is, the crown is re-cemented to the recreated preparation of the natural tooth 88.

Accordingly, while there has been shown embodiments of the present invention, it is to be understood that the invention may be embodied otherwise than is herein specifically shown and described and that within said embodiments, certain changes may be made in form and arrangement of the method without departing from the underlying ideas or principles of this invention within the scope of the Claims appended herewith.

I claim:

1. A method of use of an aqueous natural latex emulsion for protection of a natural tooth during a cure phase of a restorative resin, the method comprising the steps of:

(a) intraorally applying said emulsion to a surface of a preparation of a tooth to be restored; and (b) allowing said emulsion to cure; and (c) applying a restorative dental resin over said latex emulsion, whereby prophylaxis of natural tooth dentin from the cure-related, thermal, general toxic, and pressure effects of monomers of said resin is effected.

2. The method as recited in claim 1, in which said latex emulsion comprises a rubber emulsion.

3. The method as recited in claim 1, in which said dental resin includes resins including, without limitation, acrylic, composite-inclusive, urethane-based and bio-ceramic resins.

4. The method as recited in claim 1, in which said Step (a) includes the step of:

applying said latex emulsion to a thickness of at least eight microns, but less than about 30 microns.

5. The method as recited in claim 1, in which said step includes the step of:

allowing said latex emulsion to dry or cure to a state of substantial elasticity prior to said Step (b).

6. The method as recited in claim 5, in which said curing through evaporation of water of said aqueous emulsion, in which a satisfactory point of cure for purposes of said substantially elasticity is defined by change of color of said latex.

7. The method as recited in claim 5, further comprising the step of:

inducing curing of said latex through use of accelerating means.

8. A method of facilitating removal of a die spacer from a die model, the method comprising the steps of:

(a) applying a natural latex emulsion to a tooth die; and (b) allowing said emulsion to cure; and (c) applying a die spacer over said latex emulsion.

9. The method as recited in claim 8, further comprises the step of:

allowing said latex emulsion to dry or cure to a state of substantial elasticity prior to Step (b).

10. The method as recited in claim 9, in which said Step (c) includes the step of applying said latex emulsion to a thickness of at least 8 microns.

11. The method as recited in claim 9, in which said latex emulsion comprises a rubber emulsion.

12. The method as recited in claim 9, in which said allowing Step (a) includes:

a curing through evaporation of water of said aqueous emulsion in which a satisfactory point of cure for purposes of said substantially elasticity is defined by change of color of said latex.

13. The method as recited in claim 12, in which said allowing Step (a) includes the step of:
   inducing curing the latex emulsion through the use of accelerating means.

14. A method of use of an aqueous natural latex emulsion comprising the step of:
   applying, in one or more layers, totalling 0.2 mm to about 1.0 mm of said latex film after drying to a tooth surface area of a dental model of a tooth to be bleached, said layer applied to enlarge a dimension between a bleaching tray and the tooth surface to be bleached,
   thereby forming a fluid tight bleaching reservoir between said tooth surface area and the tray.

15. A method of using an aqueous natural latex emulsion as a protective separator, release agent, and spacer between a model of a tooth preparation and a resin used in the formation of a translucent dental on-lay, in-lay, crown, bridge, provisional, laminate, or other restoration, said method comprising the steps of:
   (a) applying a layer of prescribed dentin colored die spacer to a contact surface of said model of said restoration; and
   (b) applying a film or layer of opaque white natural latex comprising an emulsion of about 30 to about 70 percent natural rubber solids within said aqueous emulsion, in which said latex consists primarily of isoprene butyryl, over said die spacer, such application substantially covering the surface of the die spacer;
   (c) allowing said film or layer to dry to a clear, transparent state; and
   (d) applying a translucent restorative resin over said layer of latex,
whereby said coloration of said dentin colored die spacer is visible through said restorative resin, enabling a technician to better judge the accuracy of the color of the resin built up over said latex and preparation, prior to removal of the cured resin from the preparation which removal is facilitated by said layer of latex.

16. The method as recited in claim 15, in which said applying Step (b) comprises:
   applying said emulsion having about 40 to 45 percent of said solids within said aqueous solution.

17. The method as recited in claim 15, in which said applying Step (b) includes the step of applying said latex to a thickness of at least eight microns.

18. The method as recited in claim 15, in which said allowing Step (c) includes a protein and evaporative curing in which a satisfactory point of cure defined a state of substantial elasticity is characterized by a change of color of said latex material from white to transparent, within said emulsion of solids.

19. A method of using a natural latex emulsion as a protective separator, release agent or spacer between a translucent resin in the formation of a translucent restoration and a tooth on a model, comprising the steps of:

(a) applying a layer of dentin shaded die spacer to a surface of said tooth die;
   (b) applying to said die spacer a film or layer of clear natural latex comprising an emulsion of about 30 to about 70 percent natural rubber solids within an aqueous solution, in which said latex consists essentially primarily of isoprene butyryl, such application substantially covering the surface of said die spacer;
   (c) allowing said film or layer to dry to a clear, transparent state; and
   (d) applying a translucent restorative resin over said layer of latex emulsion,
whereby said coloration of said die spacer is visible through said restorative resin, enabling a technician to better judge the accuracy of the color of the resin built up over said latex and dentin colored preparation, prior to removal of the cured resin from the preparation which removal is facilitated by said layer of latex.

20. The method as recited in claim 19, in which said applying Step (b) includes applying a suspension of about 40 to 45 percent solids within said aqueous solution.

21. The method as recited in claim 19, in which said applying Step (b) includes the step of applying said latex to a thickness in the range of about eight to about thirty microns.

22. The method as recited in claim 19, in which said allowing Step (c) includes a protein and evaporative curing in which a satisfactory point of cure comprises a state of substantial elasticity is defined by a change of color of said latex material within said emulsion of solids.

23. A method of rebuilding a natural tooth preparation that broke within a dental crown, comprising the steps of:
   (a) removal of a tooth structure out of the crown;
   (b) creating a post or core from remaining tooth structure of a broken tooth;
   (c) applying a layer of natural latex film to an interior surface of the recess of said crown, after removal of a broken tooth;
   (d) after curing of the film, placing a self-cured dental resin inside of a crown over said latex film, filling the interior void space of the crown with said resin or cement;
   (e) prior to curing of said resin or core build-up material, placing said crown onto a post or core build-up;
   (f) seating and adjusting a crown restoration resultant of said Step (e);
   (g) after curing of said resin or core material, removing the restoration from the thereby newly created crown preparation;
   (h) removing or peeling said layer of latex film from said crown preparation; and
   (i) re-cementing said crown preparation to the newly created preparation.

* * * * *